United States Patent
Hahnen

(12) 
(10) Patent No.: US 6,168,586 B1
(45) Date of Patent: Jan. 2, 2001

(54) INFLATABLE CANNULA AND METHOD OF USING SAME

(75) Inventor: Kevin Hahnen, San Jose, CA (US)

(73) Assignee: Embol-X, Inc., Mountain View, CA (US)

(*) Notice: Under 35 U.S.C. 154(b), the term of this patent shall be extended for 0 days.

(21) Appl. No.: 09/130,585

(22) Filed: Aug. 7, 1998

(51) Int. Cl.[7] .................................................. A61M 31/00
(52) U.S. Cl. ............................ 604/509; 604/96; 604/506
(58) Field of Search ............................. 604/96–103, 118, 604/500, 502, 507, 508, 509

(56) References Cited

U.S. PATENT DOCUMENTS

| | | | |
|---|---|---|---|
| 4,636,195 | * 1/1987 | Wolinsky | 604/53 |
| 4,921,483 | * 5/1990 | Wijay et al. | 604/96 |
| 5,250,025 | * 10/1993 | Sosnowski et al. | 604/51 |
| 5,328,471 | * 7/1994 | Slepian | 604/101 |
| 5,419,763 | 5/1995 | Hildebrand | 604/54 |
| 5,558,644 | * 9/1996 | Boyd et al. | 604/96 |
| 5,588,961 | 12/1996 | Leone et al. | 604/21 |
| 5,766,151 | * 6/1998 | Valley et al. | 604/96 |
| 5,775,327 | 7/1998 | Randolph et al. | 128/642 |
| 5,908,407 | 6/1999 | Frazee et al. | 604/101 |
| 5,928,192 | 7/1999 | Maahs | 604/96 |

* cited by examiner

Primary Examiner—Sharon Kennedy
Assistant Examiner—Jennifer Maynard
(74) Attorney, Agent, or Firm—Lyon & Lyon LLP

(57) ABSTRACT

An expandable lumen cannula which includes an elongate tube having a proximal end, a distal end, an intermediate flexible region, and a lumen therebetween. The cannula further includes a balloon occluder mounted on the distal end of the tube. The intermediate flexible region of the tube further includes an elongate generally cylindrical balloon disposed circumferentially about the flexible region which, upon inflation, expands the luminal diameter of the intermediate region. First and second inflation ports are in fluid communication with the balloon occluder and the cylindrical balloon. The cannula may optionally include a cardioplegia port disposed within the distal region of the tube, proximal the balloon occluder and distal the generally cylindrical balloon. Methods of using such a cannula are also disclosed, particularly to provide cannulation through a minimally invasive port incision, and to thereafter displace the tissues and organs adjacent an intercostal access port upon inflation and expansion of the generally cylindrical balloon.

9 Claims, 3 Drawing Sheets

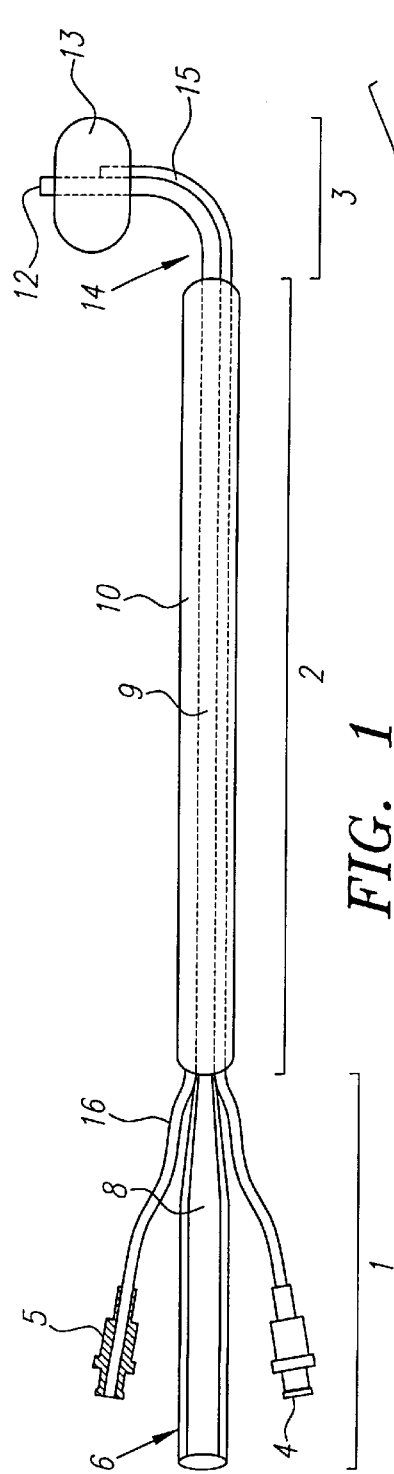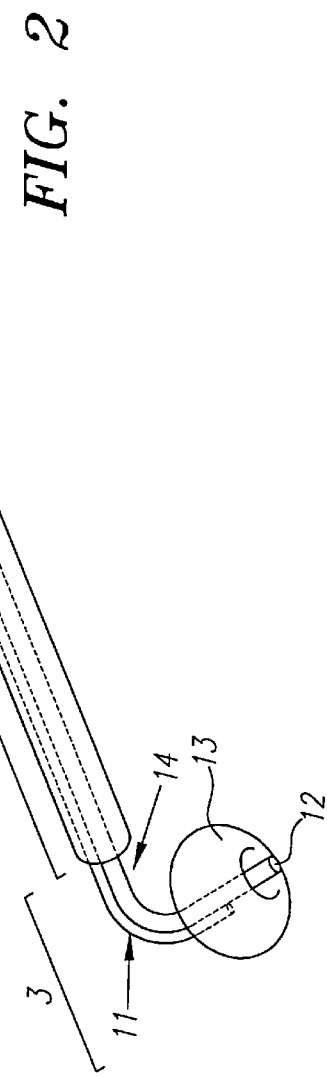
FIG. 1
FIG. 2

INFLATABLE CANNULA AND METHOD OF USING SAME

FIELD OF THE INVENTION

This invention relates generally to a cannula or catheter that can be introduced to a small port and be inflated to accommodate a large flow of fluids, or can serve as a conduit or port to apply other medical therapy, such as surgical instruments, dilatation catheters, atherectomy devices, filters, aspirators, and pressure monitors.

BACKGROUND OF THE INVENTION

Minimally invasive surgical procedures which use an endoscopic approach have been widely used in many surgical specialties, including cardiothoracic surgery. New surgical techniques and instruments have been developed especially to assist in minimally invasive coronary bypass grafting. This procedure is often performed using the port access approach where a minimal access incision is made in the intercostal space rather than the traditional midsternotomy approach, therefore minimizing trauma to the chest wall. After the incision is made, various instruments can be inserted through the incision and various tissue layers to reach the heart and great vessels. This peripherally-based system achieves aortic occlusion, cardioplegia delivery, and left ventricular decompression; thus, coronary revascularization and various cardiac procedures can be effectively performed.

Traditionally, flexible catheters or cannulas are fixed in their lumen and outside diameter size. In order to provide a large lumen for oxygenated blood flow during cardiopulmonary bypass (CPB), a traditional catheter or cannula is required to have a large diameter, therefore making insertion and tissue penetration difficult through a small port. A rigid trocar provides adequate luminal dimension; however, it is also limited in its ability to expand and provide easy access. Therefore, a need exists for a fluid delivery catheter or cannula having a flexible wall and a capability of achieving a minimal profile for entry through a small port, and having an ability to thereafter expand to accommodate a larger luminal diameter for delivery of fluid and instruments.

SUMMARY OF THE INVENTION

The present invention is particularly useful in minimally invasive coronary artery bypass grafting (CABG) since this procedure is generally performed through a small incision. In one embodiment, the invention provides a cannula comprising an elongate tube having a proximal end, a distal end, an intermediate flexible region, and a lumen. A balloon occluder is mounted at the distal end of the cannula. An elongated cylindrical balloon is disposed circumferentially about the flexible intermediate region of the tube. Each balloon occluder and the cylindrical balloon has its own inflation port. In another embodiment, the cannula has an additional lumen extending distally from the proximal end to a port proximal to the balloon occluder for delivering cardioplegic solution. In other embodiments, the cannula will further include one or more helical threads disposed about the distal end of the tube proximal to the balloon occluder and distal to the cylindrical balloon.

The present invention provides an expandable lumen cannula which assists in minimally invasive aortic cannulation. The expandable lumen cannula is inserted through a port access, advancing the distal end into the ascending aorta. The balloon occluder is then inflated followed by inflation of the cylindrical balloon, thereby increasing the diameter of the cannula lumen. Oxygenated blood then can be infused through the lumen of the cannula into the aorta distal to the balloon occluder. In alternative methods, the expanded lumen of the cannula can be used to insert medical devices for the performance of a surgical procedure within the aorta, carotid arteries, or any other internal body structure accessible by cannulation.

It will be understood that there are many advantages to using an inflatable cannula as disclosed herein. For example, the inflatable cannula of the invention can be used (1) to provide easy introduction of the cannula through a small port, (2) to provide an expanding tube that serves to gently move nearby organs and tissues out of the path during surgery, (3) to provide a conduit or port to apply other medical therapies, e.g., surgical instruments, dilatation catheters, atherectomy devices, filters, aspirators, pressure monitors, etc., (4) to provide an inflatable lumen which can accommodate large flow of fluid, e.g., oxygenated blood, into the aorta or other internal body structure, (5) to provide better contact and therefore stabilization between the cannula and the arterial wall by having cannula threads at the point of contact with the vessel wall, (6) to provide interruption of arterial flow through inflating the balloon occluder, thus minimizing damage to the arterial wall and reducing the risk of emboli dislodgment as compared to traditional clamping.

BRIEF DESCRIPTION OF THE DRAWINGS

FIG. 1 depicts an embodiment of an inflatable cannula.

FIG. 2 is an oblique view of the inflatable cannula.

DETAILED DESCRIPTION OF THE PREFERRED EMBODIMENTS

Figure 3:
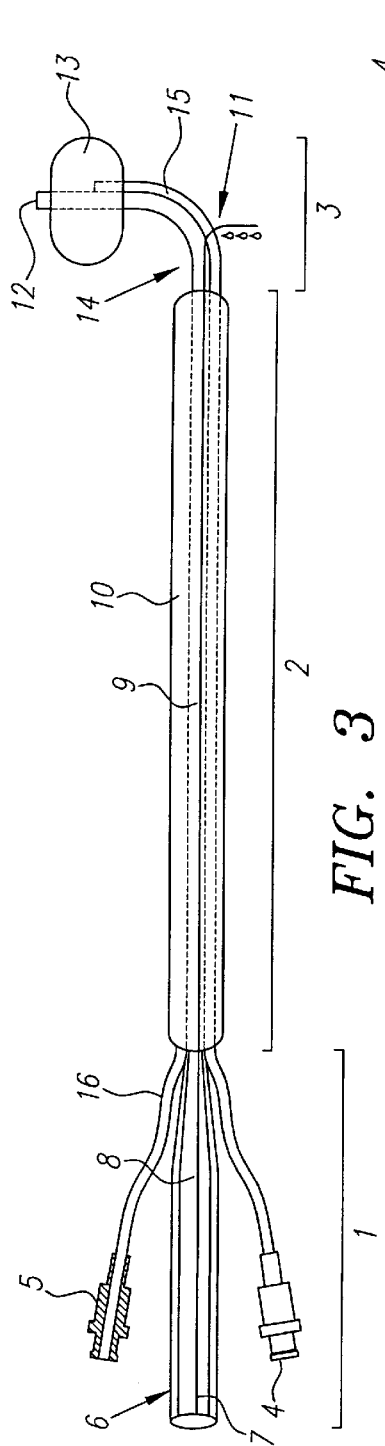
FIG. 3 depicts an embodiment of an inflatable cannula having a cardioplegia lumen and port.

The devices and methods of the invention facilitate cannulation of the aorta through a minimally invasive port access incision during minimally invasive CABG surgery. In addition, the invention facilitates thorascopic and/or endovascular delivery of cardioplegic fluid to the myocardium so as to paralyze the heart. The invention also provides devices and methods to accommodate large flow of oxygenated blood during cardiopulmonary bypass without need for peripheral access. Once the patient is on cardiopulmonary bypass, a variety of thorascopic, endovascular, or open surgical procedures may be performed, including coronary artery bypass grafting (CABG), heart valve repair, and replacement, septal defect repair, removal of atrial myxoma, patent foramen ovale closure, treatment of aneurysms, myocardial drilling, electrophysiological mapping and ablation, and correction of congenital defects.

FIG. 1 depicts an embodiment of an inflatable cannula. The cannula has a proximal region 1, intermediate region 2, and a distal region 3. The proximal region 1 has tube 6 comprising a fixed lumen 8. Inflation ports 4 and 5 arise from the junction of the proximal and intermediate region. Inflation port 4 is responsible for inflating the balloon occluder. Inflation port 5 is responsible for inflating the cylindrical balloon. Intermediate region 2 comprises the inflatable cylindrical balloon 10, lumen 9, and balloon occluder lumen 15.

FIG. 2 depicts an oblique view of the inflatable cannula. Distal region 3 includes an angulated lumen port 12 for delivery of blood products and other instruments, and the balloon occluder 13 with its communicating inflation lumen 15. Helical threads 14 are located on the distal cannula close to the junction of the intermediate region.

FIG. 3 depicts an embodiment of an inflatable cannula having an optional cardioplegia lumen 7 and cardioplegia ports 11 at the distal end.

Figure 4:
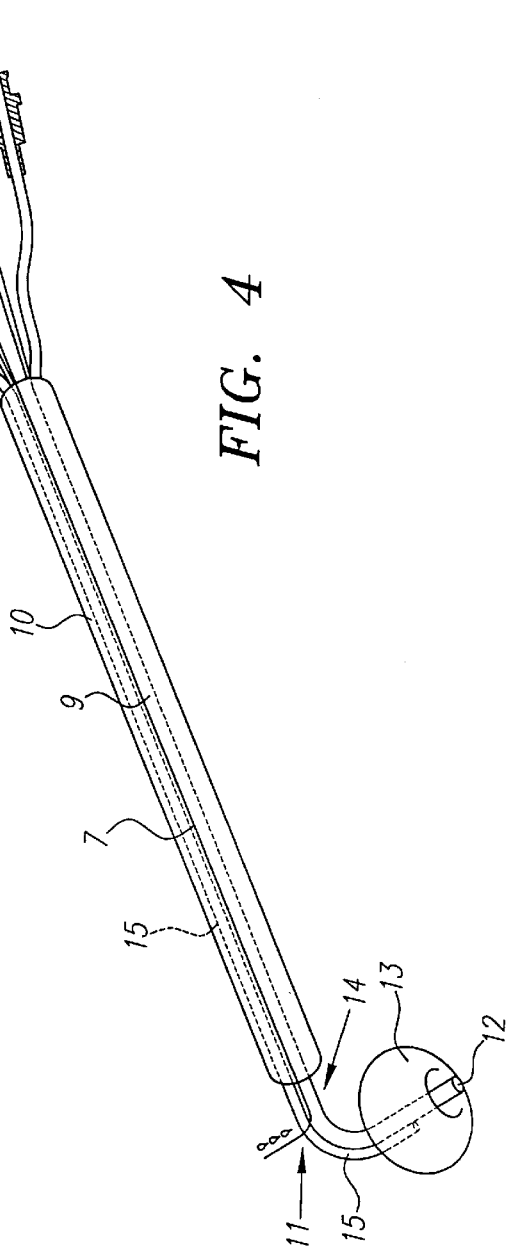
FIG. 4 is an oblique view of the inflatable cannula having the cardioplegia lumen and port.

FIG. 4 depicts an oblique view of an inflatable cannula having cardioplegia lumen 7 and cardioplegia port 11 at the distal end thereof.

Figure 5:
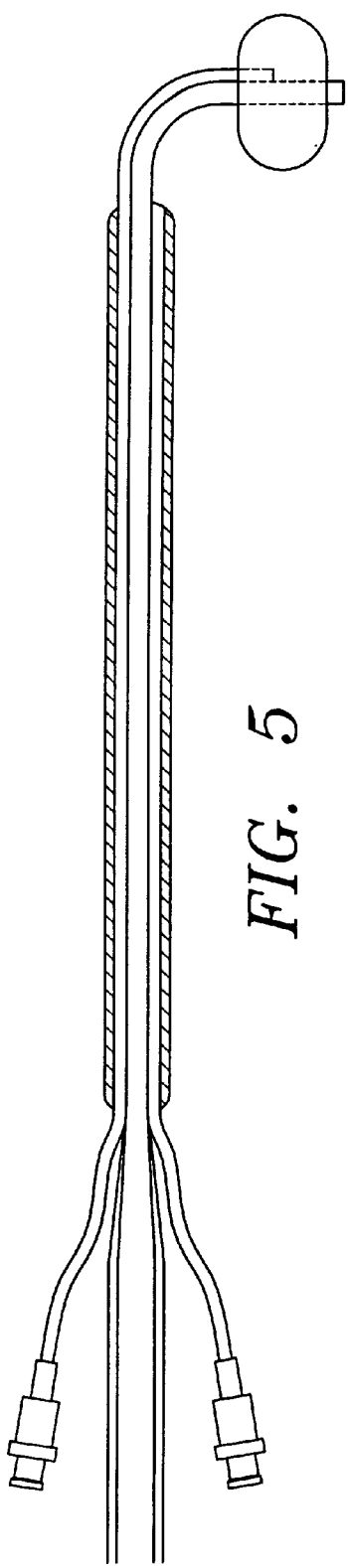
FIG. 5 depicts the deflated state of the inflatable cannula.

FIG. 5 depicts an inflatable cannula in the deflated condition. As can be seen, deflation of cylindrical balloon 10 minimizes the cross-sectional diameter of the inflatable cannula for access to a minimal incision port.

Figure 6:
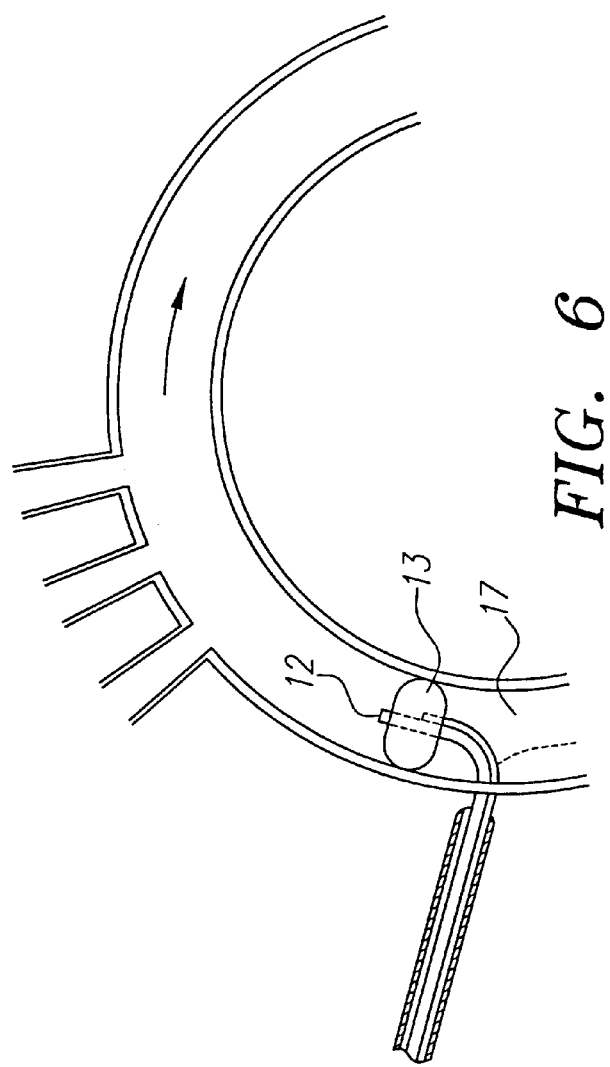
FIG. 6 depicts the position of the inflatable cannula deployed within the ascending aorta during cardiac surgery.

FIG. 6 shows an inflatable cannula deployed within the ascending aorta 17 during cardiac surgery. Balloon occluder 13 provides a gentle seal against the aortic wall. Blood products or instruments can be delivered through the end port 12 of the cannula downstream to the aorta, while cardioplegia can be delivered through cardioplegia port 11 upstream to the heart.

The length of the intermediate region 2 will generally be between 10–20 centimeters, more preferably between 12 and 15 centimeters, with a tube O.D. between 0.3 and 2.0 centimeters, more preferably 0.4–1.0 centimeters, more preferably 0.5–0.7 centimeters, more preferably approximately 0.6 centimeters. In certain embodiments, the cannula will have a circular cross-section. In other embodiments, the cannula will have an oval cross-sectional shape to more easily fit through the ribs, or it may have any other suitable shape. The inner diameter of lumen 9, when expanded, will generally be between 0.2 and 2.0 centimeters, more preferably 0.3–1.0 centimeters, more preferably 0.4–0.8 centimeters. The length of proximal region 1 will generally be between 2 and 10 centimeters, more preferably about 5 centimeters. The tube diameter and proximal region 1 is generally 0.3–1.0 centimeters, while the diameter of lumen 8 in proximal region 1 is about 0.2–0.8 centimeters. In distal region 3, when expanded, the balloon occluder will generally have a diameter between 1 centimeter and 2.5 centimeters, more preferably between 1.5 and 2.0 centimeters. The foregoing ranges are set forth solely for the purpose of illustrating typical device dimensions. The actual dimensions of a device constructed according to the principles of the present invention may obviously vary outside of the listed ranges without departing from those basic principles.

It is contemplated that the inflatable cannula disclosed herein will be used to perform any of the procedures including coronary artery bypass surgery, valve repair, septal defect repair, and thoracic aortic aneurysm (TAA) repair. A typical coronary artery bypass surgery (CABG) using minimally invasive procedures and the cannula disclosed herein generally begins with incubation of the patient after induction of anesthesia as explained in Reichenspurner et al., *Annals of Thoracic Surgery* 65:413–419 (1998), incorporated herein by reference. The right internal jugular vein is punctured using a 9 French introduction system for later insertion of the endopulmonary vent catheter. The patient is placed in a supine position. A small (6–8 centimeter; medium 7 centimeter) incision is made parasternally between the ribs, usually on top of the fourth rib. During dissection and removal of the cartilagenous part of the fourth rib, left internal mammary artery (LIMA) is dissected free. Thoroscopic preparation of the LIMA is also accomplished through three small lateral chest ports. When complete visualization of the LIMA is not possible through the mini-thoracotomy, the inflatable cannula can then assist in the above endoscopic dissection of LIMA by its ability to accommodate instruments through its expandable lumen. As the LIMA is being prepared, a 21 French venous cannula is inserted into the femoral vein and positioned into the right atrium using transesophageal echocardiography (TEE).

Before the initiation of cardiopulmonary bypass (CPB), the inflatable cannula can be inserted through a small port and guided into the ascending aorta using thoroscopy and TEE. A Swan-Ganz catheter for pressure monitoring is often inserted through the right internal jugular vein.

After LIMA is prepared for anastomosis, CPB is initiated and the balloon occluder is inflated with approximately 15–30 cc of diluted radiological contrast medium using fluoroscopy and TEE. The balloon occluder is generally placed about 2 centimeters above the aortic valve with careful monitoring of the right radial artery pressure to avoid occlusion of the brachiocephalic trunk by the endo-aortic balloon. The cylindrical balloon is then inflated to expand the luminal diameter of the cannula to accommodate oxygenated blood for CPB. In this manner, the deflated cannula passes through a small port, and is thereafter expanded by inflation, thereby displacing adjacent tissues and organs to increase luminal diameter of the cannula. After exact positioning of the balloon, cardioplegia can be administered through the optional cardioplegia port at the distal region of the inflatable cannula. Once cardioplegic arrest is achieved, an end-to-end anastomosis is performed of the LIMA to the left anterior descending coronary artery (LAD). On completion of anastomosis, the balloon occluder and the cylindrical balloon are deflated, and the cannula is removed. The heart is reperfused and the patient is weaned from CPB. After hemostasis is obtained, the femoral cannula is removed, one chest tube is inserted, and the thoracic and femoral incisions are closed.

Similar steps as described above for minimally invasive CABG can be employed in aortic or mitral valvular replacement. The inflatable cannula is inserted through a small chest port to reach the ascending aorta. After the balloon occluder is inflated, the cylindrical balloon is inflated to expand the luminal diameter of the cannula to accommodate large flow of oxygenated blood from the CPB machine. After CPB is initiated, the damaged aortic or mitral valve can be excised and a prosthetic or porcine valve can then be sutured in place. After the valve replacement is complete, the balloon occluder and the cylindrical balloon are deflated and removed. The patient is weaned from CPB, a chest tube is placed, and the femoral and chest incisions are closed.

Atrial septal defect (ASD) and ventricular septal defect (VSD) can also be repaired in a similar fashion using the inflatable cannula disclosed herein. Again, the inflatable cannula is inserted through a small chest port to reach the ascending aorta. The cylindrical balloon is inflated following inflation of the balloon occluder to provide expanded luminal diameter of the cannula to accommodate large flow of oxygenated blood from the CPB machine. After CPB is initiated, cardiac incision is made to expose the ASD or VSD. A mesh is sutured securely around the defect, and the incision on the heart is closed. The inflatable cannula is removed after the balloon occluder and the cylindrical balloon are deflated. After the patient is weaned from CPB, the chest and femoral incisions are closed.

The inflatable cannula can also assist in repair of thoracic aortic aneurysm (TAA) by providing an expanded conduit for the oxygenated blood from the CPB machine. After sternotomy, the expandable cannula can be inserted distal to the aneurysm and inflated to provide an expanded lumen. The diseased aneurysmal aorta is resected and replaced with collagen saturated Dacron™ graft. The balloons on the cannula are then deflated and the cannula is withdrawn after the patient is weaned from CPB.

In various pediatric cardiac surgeries, such as ASD, truncous arteriosis, tetralogy of Fallot, anomalous coronary artery, Ebstein's malformation of the tricuspid valve, heart/ lung transplantation and total anomalous pulmonary vein repair, CPB is commonly indicated post-operatively due to a low cardiac output state. The inflatable cannula can easily be left in place post-operatively to provide easy access to the CPB.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method of minimally invasive aortic cannulation, comprising the steps of:

providing an expandable lumen cannula comprising an elongate tube having a proximal end, a distal end, an intermediate flexible region, and a lumen therebetween, the elongate tube further including an elongate generally cylindrical balloon disposed circumferentially about the flexible intermediate region of the tube;

inserting the expandable lumen cannula through a port access, and advancing the distal end of the cannula into the ascending aorta;

positioning the cylindrical balloon within the port access;

inflating the cylindrical balloon, thereby displacing adjacent tissues to increase the outer diameter of the cannula; and infusing fluid through the lumen of the cannula into the aorta.

2. The method of claim 1, wherein the elongate tube further comprises a balloon occluder mounted on the distal end, and wherein the method further comprises the step of inflating the balloon occluder.

3. The method of claim 2, wherein the fluid is oxygenated blood.

4. The method of claim 3, wherein the oxygenated blood is infused into the aorta distal the balloon occluder.

5. The method of claim 1, further comprising the step of performing cardiopulmonary bypass.

6. The method of claim 1, further comprising the step of performing coronary artery bypass graft.

7. The method of claim 1, further comprising the step of performing a valve replacement.

8. The method of claim 1, further comprising the step of performing thoracic aortic aneurysm repair.

9. The method of claim 1, further comprising the step of performing septal defect repair.

* * * * *

UNITED STATES PATENT AND TRADEMARK OFFICE
CERTIFICATE OF CORRECTION

PATENT NO.     : 6,168,586 B1                                                    Page 1 of 1
DATED          : January 2, 2001
INVENTOR(S)    : Hahnen It is certified that error appears in the above-identified patent and that said Letters Patent is hereby corrected as shown below:

<u>Title page,</u>
Item [56], References Cited, please add the following references:

-- U.S. PATENT DOCUMENTS
5,797,960     08/1998     Stevens et al. .......606/213

<u>Column 3,</u>
Line 59, change "Reichenspumer" to -- Reichenspurner --.

Signed and Sealed this

Thirteenth Day of August, 2002

*Attest:*

*Attesting Officer*

JAMES E. ROGAN
*Director of the United States Patent and Trademark Office*